United States Patent
Shannon et al.

(10) Patent No.: US 7,988,824 B2
(45) Date of Patent: Aug. 2, 2011

(54) TISSUE PRODUCT HAVING A TRANSFERABLE ADDITIVE COMPOSITION

(75) Inventors: Thomas Gerard Shannon, Neenah, WI (US); Lisa Ann Flugge-Berendes, Appleton, WI (US); Frederick J. Lang, Neenah, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 749 days.

(21) Appl. No.: 11/304,985

(22) Filed: Dec. 15, 2005

(65) Prior Publication Data

US 2007/0137812 A1     Jun. 21, 2007

(51) Int. Cl.
  *D21H 17/24*  (2006.01)
  *D21H 17/25*  (2006.01)
  *D21H 17/33*  (2006.01)
  *D21H 27/30*  (2006.01)

(52) U.S. Cl. ........ 162/125; 162/123; 162/146; 162/158; 162/164.1; 162/172; 162/175; 162/176; 162/184; 428/535

(58) Field of Classification Search .................. 162/123, 162/125, 132, 146, 158, 164.1, 172, 175, 162/176, 184; 428/436, 535
See application file for complete search history.

(56) References Cited

U.S. PATENT DOCUMENTS

| | | |
|---|---|---|
| 1,102,203 A | 6/1914 | Scott |
| 1,775,998 A | 9/1930 | Greenberg |
| 1,960,192 A | 5/1934 | Howard |
| 3,814,096 A | 6/1974 | Weiss et al. |
| 4,426,418 A | 1/1984 | Coleman et al. |
| 4,440,597 A | 4/1984 | Wells et al. |
| 4,481,243 A | 11/1984 | Allen |
| 4,514,345 A | 4/1985 | Johnson et al. |
| 4,528,239 A | 7/1985 | Trokhan |
| 4,529,480 A | 7/1985 | Trokhan |
| 4,601,938 A | 7/1986 | Deacon et al. |
| 4,610,678 A * | 9/1986 | Weisman et al. ............. 604/368 |
| 4,950,545 A | 8/1990 | Walter et al. |
| 4,987,632 A | 1/1991 | Rowe et al. |
| 5,098,522 A | 3/1992 | Smurkoski et al. |
| 5,227,242 A | 7/1993 | Walter et al. |
| 5,230,776 A | 7/1993 | Andersson et al. |
| 5,260,171 A | 11/1993 | Smurkoski et al. |
| 5,275,700 A | 1/1994 | Trokhan |
| 5,328,565 A | 7/1994 | Rasch et al. |

(Continued)

FOREIGN PATENT DOCUMENTS

WO   WO 9624722 A1   8/1996

(Continued)

OTHER PUBLICATIONS

PCT Search Report for International Appl. No. PCT/US2006/030035 dated Feb. 2, 2007.

*Primary Examiner* — Matthew J Daniels
*Assistant Examiner* — Dennis Cordray
(74) *Attorney, Agent, or Firm* — Dority & Manning, P.A.

(57) ABSTRACT

A tissue product is disclosed containing an additive composition. The additive composition may be, for instance, a composition designed to provide benefits to a user's skin. In accordance with the present disclosure, the additive composition is located in a target delivery zone on a base web. The base web is modified in the target delivery zone so that the additive composition more efficiently transfers to an opposing surface during use.

34 Claims, 5 Drawing Sheets

U.S. PATENT DOCUMENTS

| | | |
|---|---|---|
| 5,334,289 A | 8/1994 | Trokhan et al. |
| 5,353,521 A | 10/1994 | Orloff |
| 5,431,786 A | 7/1995 | Rasch et al. |
| 5,496,624 A | 3/1996 | Stelljes, Jr. et al. |
| 5,500,277 A | 3/1996 | Trokhan et al. |
| 5,514,523 A | 5/1996 | Trokhan et al. |
| 5,554,467 A | 9/1996 | Trokhan et al. |
| 5,566,724 A | 10/1996 | Trokhan et al. |
| 5,598,642 A | 2/1997 | Orloff et al. |
| 5,607,551 A | 3/1997 | Farrington, Jr. et al. |
| 5,624,724 A | 4/1997 | Relly |
| 5,624,790 A | 4/1997 | Trokhan et al. |
| 5,628,876 A | 5/1997 | Ayers et al. |
| 5,637,194 A | 6/1997 | Ampulski et al. |
| 5,667,636 A | 9/1997 | Engel et al. |
| 5,772,845 A | 6/1998 | Farrington, Jr. et al. |
| 6,096,169 A | 8/2000 | Hermans et al. |
| 6,103,063 A | 8/2000 | Oriaran et al. |
| 6,143,135 A | 11/2000 | Hada et al. |
| 6,217,707 B1 | 4/2001 | Garvey et al. |
| 6,316,687 B1 * | 11/2001 | Davis et al. .................. 604/372 |
| 6,498,284 B1 * | 12/2002 | Roe ................................ 604/381 |
| 2002/0001726 A1 * | 1/2002 | Burghardt et al. ............ 428/447 |
| 2003/0098135 A1 * | 5/2003 | Ross et al. ..................... 162/123 |
| 2003/0114812 A1 * | 6/2003 | Braverman et al. ........... 604/367 |
| 2004/0033744 A1 * | 2/2004 | Eden et al. .................... 442/118 |
| 2004/0099388 A1 * | 5/2004 | Chen et al. .................... 162/134 |
| 2004/0118531 A1 * | 6/2004 | Shannon et al. .............. 162/109 |
| 2004/0118532 A1 | 6/2004 | Sarbo et al. |
| 2004/0163785 A1 * | 8/2004 | Shannon et al. .............. 162/158 |
| 2004/0181198 A1 * | 9/2004 | Farbrot et al. ................. 604/367 |
| 2005/0145353 A1 * | 7/2005 | Troxell et al. ................. 162/118 |
| 2005/0241789 A1 | 11/2005 | Reddy |

FOREIGN PATENT DOCUMENTS

| | | |
|---|---|---|
| WO | WO 9624723 A1 | 8/1996 |
| WO | WO 0072819 A1 | 12/2000 |
| WO | WO 0149933 A1 | 7/2001 |
| WO | WO 2004080358 A1 | 9/2004 |

* cited by examiner

TISSUE PRODUCT HAVING A TRANSFERABLE ADDITIVE COMPOSITION

BACKGROUND OF THE INVENTION

Absorbent tissue products such as facial tissues, bath tissues, paper towels and so forth have been used to absorb fluids on the skin and leave the skin dry. Frequent use of these products may, however, tend to irritate the skin over time. To reduce skin irritation, tissue products have included additives applied to the tissue surfaces to reduce or eliminate irritated skin during heavy use periods. The additives can enhance sheet softness perceptions by reducing the stiffness of the sheet, making it more drapeable, or by providing lubricity, helping the sheet glide across the surface of the skin.

In some embodiments, additives may be applied to the tissue product that are intended to be transferred to the user. For example, vitamins, plant extracts, medications, antimicrobial compounds, and the like may be applied to a tissue sheet in order to be transferred to a consumer upon use. Applying these compositions to a tissue or wiping product provides a certain level of convenience for the consumer.

For a benefit to be realized, however, a certain minimum amount of the composition must be transferred to a target surface for the composition to be efficacious. When the compositions are applied to tissue products, however, only a minimal amount of the total composition applied to the sheet is actually transferred to the target surface. Thus, tissue products containing a topical composition typically have a significantly poorer efficiency than when the composition is delivered in a bottled lotion that is applied to the skin separately from the tissue product. Efficiency here can be defined as the ratio of amount of the substance transferred to the target surface to the amount of composition applied to the applicator. In the case of a tissue treated with an additive the treated tissue becomes the applicator. In the case of a bottled product the applicator is the object used to transfer to the target surface and may be a finger, a hand, etc.

In addition, manufacturing systems for topically applying the beneficial compositions are typically designed to apply the composition over the entire sheet, although only a small area of the sheet is actually used to wipe the surface. Thus, much of the functional composition is wasted when the product is disposed. In addition, application of the composition across the entire surface of the wiping product may compromise other attributes of the tissue product, such as its ability to rapidly absorb and remove fluids, dirt, etc.

In view of the above, there is currently a need for a tissue product that is capable of delivering efficacious amounts of a beneficial composition to an adjacent surface, such as the user's skin. There is also a need for a tissue product containing a beneficial composition in which the composition does not compromise the inherent properties of the product, such as the wicking and absorption characteristics of the product.

SUMMARY OF THE INVENTION

The present disclosure is generally directed to tissue products that include an additive composition designed to provide, for instance, clinical benefits to the user. More particularly, the additive composition is designed to be transferred to a user in a more efficient manner than many prior art products.

Delivery of the additive composition from the tissue product to a user is enhanced by incorporating a target delivery zone into the product. The target delivery zone may contain the additive composition in relatively high amounts. Transfer of the additive composition is further enhanced by modifying the substrate within the target delivery zone in order to reduce the affinity of the substrate for the additive composition. By using a localized target delivery zone, the fluid absorbency and wicking characteristics of the remainder of the tissue product are not adversely affected by the presence of the additive composition. Thus, the tissue product may be used not only to transfer the additive composition to a user, but also may be used as a wiping product.

In one embodiment, for instance, the present disclosure is directed to a tissue product that includes a base web containing cellulosic fibers. The base web may have a dry bulk density of at least about 3 cc/g and may contain, for instance, softwood fibers, hardwood fibers or mixtures thereof. In other embodiments the base web may have a bulk density of at least about 4 cc/g such as from about 5 cc/gram to about 14 cc/gram.

A target delivery zone is located on a first side of the base web. The target delivery zone may comprise a portion of the total surface area of the first side. An additive composition is applied to the target delivery zone on the base web. The additive composition is intended to be transferred to an adjacent surface when the tissue product is used. For example, the additive composition may comprise a lotion that is intended to provide clinical benefits to the skin of a user.

In accordance with the present disclosure, in one embodiment, the first side of the base web is modified at least in the target delivery zone in a manner that causes greater amounts of the additive composition to transfer to an opposing surface when the tissue product is wiped against the opposing surface. The base web may be modified using various methods and techniques. For example, if the additive composition is hydrophilic in nature, the first side of the base web may be modified so as to render the target delivery zone hydrophobic prior to adding the additive composition to the base web. In another embodiment both the first and second sides of the base web are modified in the target delivery zone in a manner that causes greater amounts of the additive composition to transfer to an opposing surface when the tissue product is wiped against the opposing surface. In this embodiment the target delivery zone comprises less than 70% of the total surface area of either side of the sheet and preferably comprises less than 30% of the total surface area of either side of the sheet. In this manner the absorbent properties of the untreated sheet are maintained.

In one embodiment, for instance, the first side of the base web may be modified by adhering a polymeric film or a nonwoven web containing synthetic fibers to the base web at least in the target delivery zone. The polymeric film or nonwoven web may be made from a synthetic polymer, such as a polyolefin. Examples of suitable polyolefins include, but is not limited to, polyethylene and polypropylene. In another embodiment the film is comprised of a biodegradable film material sourced from renewable or non-renewable (petroleum) resources. Examples of natural resins (or biopolymers) suitable for the films include, but is not limited to, films made from starch and cellulose as well as materials such as polyhydroxyalcanoates (PHA) and. Polylactides (PLA) formed by polymerization of lactic acid. Examples of biodegradable materials made from non-renewable resources include polycaprolactone and modified polyethylenes and polypropylene films. When a nonwoven web is used, the nonwoven web may be a spunbond web, a meltblown web or the like. The nonwoven web or film may be applied to the same side of the base web as the additive composition. Alternatively, the nonwoven web or film may be adhered to the opposite side of the nonwoven web. In this embodiment, the base web may be perforated in between the additive composition and the nonwoven web or film.

In an alternative embodiment, the first side of the base web may be modified by applying a sizing agent, a wax or a resin to the base web.

In general, the target delivery zone only comprises a portion of the total surface area of the sides of the base web to which the target delivery zone is present. For example, the target delivery zone may comprise less than about 70% of the area of the first side of the base web, such as from about 10% to about 40% of the surface area of the side of the base web on which the target delivery zone is present. The target delivery zone may be visually differentiated from the remainder of the first side of the base web if desired. Depending upon the additive composition, the target delivery zone may also be surrounded by a barrier to prevent migration of the additive composition in the x-y direction of the sheet.

The additive composition may comprise any suitable composition where it is desired to transfer the composition onto an adjacent surface. For example, in various embodiments, the additive composition may comprise a skin lotion. The additive composition, for example, may contain a silicone. In one embodiment, the additive composition may comprise a blended wax, an oil and an alcohol. The additive composition may be present in the target delivery zone in an amount from about 2 gsm to about 150 gsm or greater. For instance, the additive composition may be present in the target delivery zone in an amount from about 5 gsm to about 250 gsm such as from about 10 gsm to about 200 gsm. In other embodiments, the additive composition is present in the target delivery zone in an amount of at least 25 gsm. The tissue product may comprise, for instance, a bath tissue, a facial tissue, a napkin, a paper towel, or the like. The tissue product may comprise a single ply product or a multi-ply product. In one embodiment, the tissue product may include four quadrants. The target delivery zone may be present in one or two of the quadrants.

In an alternative embodiment, the tissue product may include at least one fold line along which the base web is folded. The target delivery zone may be located along the fold line such that the additive composition is folded onto itself when the base web is folded. In another alternative embodiment, the target delivery zone is offset from a portion of the tissue so as not to interfere with the tissue's ability to cleanse or absorb. In general, the center of the sheet will be used for cleansing and absorption such that the target delivery zones are offset from the center, located along the periphery of the sheet.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

Figure 1A:
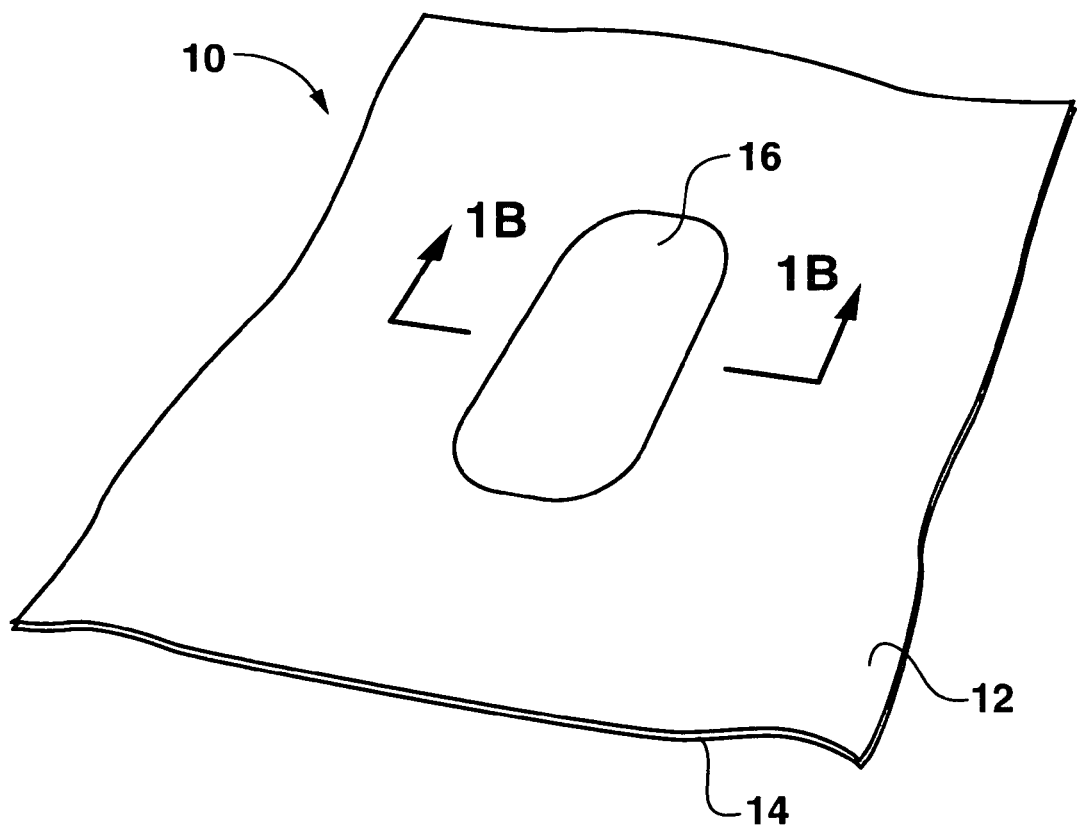
FIG. 1A is a perspective view of one embodiment of a tissue product made in accordance with the present invention.

Repeat use of reference characters in the present specification and drawings is intended to represent the same or analogous features or elements of the present invention.

DETAILED DESCRIPTION

It is to be understood by one of ordinary skill in the art that the present discussion is a description of exemplary embodiments only, and is not intended as limiting the broader aspects of the present invention.

In general, the present disclosure is directed to tissue products containing an additive composition that is intended to be transferred to an adjacent surface during use of the product. The additive composition is located within a target delivery zone or target delivery zones creating treated areas and untreated areas on the product. The untreated areas are essentially free of the additive composition. In this manner, the additive composition does not adversely interfere with the ability of the untreated areas to absorb liquids and perform other basic functions of the tissue product.

In accordance with the present disclosure, the base sheet where the target delivery zone is located is also modified prior to applying the additive composition in order to enhance the ability of the product to transfer the additive composition onto an adjacent surface. The base sheet in the target delivery zone, for instance, may be modified by providing the surface with a different surface energy or porosity. In one embodiment, for instance, the base sheet in the target delivery zone may be rendered hydrophobic, especially when the additive composition is hydrophilic. In particular, the present inventors have found that hydrophilic compositions transfer more effectively from a hydrophobic surface than from a hydrophilic surface.

In various embodiments as will be described in greater detail below, for example, the base sheet in the target delivery zone may be modified by adhering a nonwoven web, a film, a sizing agent, a wax, a resin, and the like to the base sheet.

By only applying the additive composition to the target delivery zone, if desired, relatively high concentrations of the additive composition may be applied to the delivery zone. Again, this allows for maximum transfer of the additive composition to an adjacent surface.

If desired, the target delivery zone containing the additive composition may be clearly differentiated from the untreated areas of the base sheet. The differentiation may be achieved, for example, via a sensory device that makes the target delivery zone immediately detectable from visual inspection or through touch. For example, in one embodiment, a dye may be incorporated into the additive composition or otherwise into the target delivery zone so that the target delivery zone is visible upon inspection of the tissue product.

Figure 1B:
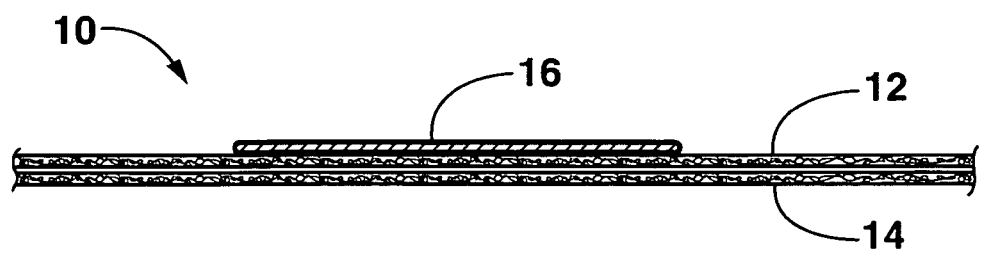
FIG. 1B is a cross-sectional view of the tissue product shown in FIG. 1A.

Referring to FIGS. 1A and 1B, one embodiment of a tissue product generally 10 made in accordance with the present invention is shown. As illustrated, the tissue product 10 includes, in this embodiment, a first ply 12 and a second ply 14. It should be understood, however, that the teachings of the present invention may also be used in conjunction with single ply tissue products or tissue products containing more than two plies.

As shown particularly in FIG. 1A, the first ply 12 of the tissue product 10 defines a target delivery zone 16. The target delivery zone contains an additive composition and is configured to efficiently transfer the additive composition onto an adjacent surface when the tissue product is contacted with the surface. As shown, the target delivery zone 16 only occupies a portion of the total surface area of the base web 12. For example, the target delivery zone 16 may comprise less than about 70% of the surface area of the side of the sheet where the target delivery zone is located, such as less than about 50% of the surface area of the sheet. In other embodiments, the target delivery zone 16 may comprise less than about 30% of the total surface area of the sheet, such as less than about 20% of the surface area of the sheet. Further, the tissue product 10 may include only a single target delivery zone 16 as shown in FIG. 1A, or may include multiple target delivery zones. The multiple target delivery zones may appear on the same side of the tissue product or on opposite sides. In another embodiment, where multiple target delivery zones are present on the sheet, the target delivery zones may contain different additives that supply separate benefits to the user. In this way it is possible to deliver from a single sheet additives that may be incompatible with each other.

Because the target delivery zone only covers a portion of the entire surface area of the tissue product, various advantages and benefits are realized. For example, by only occupying a portion of the total surface area of the base sheet, the areas of the base sheet not treated with the additive composition may remain capable of absorbing liquids unhindered by the additive composition. Thus, the tissue product cannot only effectively absorb fluids but can also apply the additive composition to an adjacent surface with a high level of efficiency.

In accordance with the present disclosure, in order to improve the ability of the tissue product 10 to transfer an additive composition to an adjacent surface, the base sheet 12 as shown in FIGS. 1A and 1B is modified at least in the target delivery zone. Specifically, the base web is modified in a manner that causes greater amounts of the additive composition to transfer to an opposing surface. The base sheet 12 may be modified over the entire surface area of the base sheet or may be modified only where the target delivery zone 16 is located.

Modifying the base sheet in a manner that causes greater amounts of the additive composition to transfer to an opposing surface may in some embodiments adversely interfere with the ability of the base sheet to absorb liquids. Thus, in one embodiment, when substantially the entire surface area of the base web 12 is modified, it may be beneficial to include further tissue plies as shown in FIG. 1A. In this manner, the second ply 14 is available for fluid absorption and retention. In still other embodiments, a third ply may be contained within the first ply 12 and the second ply 14. The third or middle ply may not only further increase the water absorption characteristics of the product but may also serve as a barrier ply.

The manner in which the base sheet 12 is modified depends on various factors and the particular application. For example, the modification may depend upon the construction of the base sheet itself or on the components contained in the additive composition. In one embodiment, the base sheet 12 is modified within the target delivery zone 16 in a manner such that the additive composition has little or no adhesion to the base sheet in the target delivery zone.

In one particular embodiment, for instance, a coating may be applied to the base sheet in order to modify the base sheet in the target delivery zone. For instance, a sizing agent, a wax or a resin may be applied to the base sheet 12 at least within the target delivery zone 16. Suitable agents for creating hydrophobic areas in the sheet may be selected from agents known for imparting hydrophobicity to sheets including sizing agents such as acid rosin, alkenyl ketene dimers, alkenyl succinic anhydride, alkyl ketone dimers, and alkenol ketene dimers and are preferably applied externally to the sheet to allow for creation of treated and untreated areas. Examples of other suitable sizing agents are described in "Papermaking and Paper Board Making", $2^{nd}$ ed., Volume III, edited by R. G. MacDonald and J. N. Franklin, incorporated herein by reference. Once the base sheet 12 is coated with one of the above materials, an appropriate additive composition may be applied to the base sheet using any suitable technique. For instance, the additive composition may be printed on the base sheet, slot coated on the base sheet, sprayed on the base sheet, or the like.

In general, any suitable additive composition may be applied to a tissue product in accordance with the present disclosure. The specific formulation is not overly critical and can comprise any formulation known in the art. A non-exhaustive list of different additives that may be present in the additive composition include, for example, anti-acne actives, antimicrobial actives, antifungal actives, antiseptic actives, antioxidants, cosmetic astringents, drug astringents, deodorants, emollients, external analgesics, film formers, fragrances, humectants, natural moisturizing agents and other skin moisturizing ingredients known in the art such as lanolin, skin conditioning agents, skin exfoliating agents, skin protectants, and sunscreens. Particular examples of additives include, for instance, Vitamin E and Aloe Vera extracts. Additional additives include polysiloxanes such as dimethicone, cyclodimethicones, amidodimethicones, silicone glycols and the like.

In addition to the above additives, various other ingredients may be present in the additive composition. For example, the additive composition may contain preservatives, antifoamers, and surfactants.

In one embodiment, the basesheet may also contain one or more softeners. The softener may be, for instance, a polysiloxane that makes a tissue product feel softer to the skin of a user. Suitable polysiloxanes that may be used in the present invention include amine, aldehyde, carboxylic acid, hydroxyl, alkoxyl, polyether, polyethylene oxide, and polypropylene oxide derivatized silicones, such as aminopolydialkylsiloxanes. When using an aminopolydialkysiloxane, the two substituent radicals may be methyl groups, ethyl groups, and/or a straight branched or cyclic carbon chain containing from about 3 to about 8 carbon atoms. Some commercially available examples of polysiloxanes include WETSOFT CTW, AF-21, AF-23 and EXP-2025G of Kelmar Industries, Y-14128, Y-14344, Y-14461 and FTS-226 of the Crompton Corporation, and Dow Corning 8620, Dow Corning 2-8182, Dow Corning HMW2220 and Dow Corning 2-8194 of the Dow Corning Corporation. In some embodiments the basesheet may comprise ingredients found in the additive composition for the purpose of modifying the physical and tactile properties of the basesheet but are not intended to be delivered to the surface being wiped by the article.

Merely for exemplary purposes, the following is one example of an additive composition that may be used in accordance with the present disclosure. The following additive composition is well suited for healing irritated skin or for preventing the skin from becoming irritated. The following formulation, for instance, is well suited for use on a facial tissue to protect one's nose.

| Ingredient | Amount |
| --- | --- |
| Mineral Oil | 14-50% |
| Ceresin Wax | 15-20% |
| Stearyl Alcohol | 15-20% |
| Isopropyl Palmitate | 1-5% |
| Aloe Extract | 0-1.0% |
| Vitamin E Acetate | 0-1% |
| Sunflower Oil | 0-10% |
| Hydrogenated Vegetable Oil | 0-10% |
| Active Ingredients | 1-35% |
| Dimethicone | 1-6% |
| Petrolatum | 15-35% |

The amount of additive composition applied to the tissue ply 12 as shown in FIG. 1A may also vary depending upon the particular application. In general, the amount of additive composition applied to the tissue ply 12 can be sufficient so that an effective or desired amount of the composition is transferred to an adjacent surface. Of particular advantage, since only a portion of the surface area of the base sheet 12 is treated with the additive composition, relatively high amounts on a per area basis may be applied to the base sheet. In this manner, greater amounts of the additive composition will be transferred during product use.

In general, the additive composition may be contained in the target delivery zone in an amount from about 2 gsm to about 150 gsm or greater. For instance, the additive composition may be present on the base sheet in an amount from about 5 gsm to about 50 gsm. In one particular embodiment, the additive composition may be present on the base sheet in an amount of at least 25 gsm.

In the past, it was common to apply lotion compositions to tissue products in amounts of approximately 10% by weight. The lotion compositions, however, were applied over the entire surface area of the tissue product. The following is an example to show that by only applying the additive composition to a target delivery zone, the additive composition is used in a more efficient manner. For instance, Table 1 below compares a conventional two or three ply facial tissue containing an additive composition in comparison to a similarly constructed facial tissue containing the additive composition in a target delivery zone. In both examples in the table, the tissue sheets have a standard size of 8.5" by 8.5" and have the additive composition applied to the tissue such that the total additive composition in the sheet is 8% by weight. In the example made according to the present disclosure, the target delivery zone has dimensions of 2.75" by 2.75".

TABLE 1

|  | Typical 2 or 3-ply facial tissue | Invention Tissue Example |
| --- | --- | --- |
| Surface area (cm$^2$) | 932 | 932 |
| Tissue weight (g) | 2.182 | 2.182 |
| Tissue Basis Weight (g/m$^2$) | 23.4 | 23.4 |
| % lotion | 8% | 8% |
| lotion weight (g) | 0.17 | 0.17 |
| Lotion Area (cm$^2$) | 932 | 50 |
| lotion/area (g/m$^2$) | 1.9 | 34.9 |
| % lotion in treated area | 8% | 149% |

TABLE 1-continued

As shown above, the amount of the additive composition in the target delivery zone is significantly higher than when the additive composition is applied over the entire surface area. Since the additive composition is concentrated in a certain area, more of the additive composition is transferred to an adjacent surface when the tissue product is used.

In general, any suitable tissue product may be treated in accordance with the present invention. In general, tissue products typically have relatively high bulk characteristics. For example, tissue products may have a dry bulk of greater than about 2 cc/g, such as greater than about 4 cc/g, such as greater than about 6 cc/g. In still other embodiments, the bulk of the tissue webs may be greater than about 7 cc/g, such as greater than about 9 cc/g.

For the tissue sheets of the present invention, both creped and uncreped webs may be used. Uncreped tissue production is disclosed in U.S. Pat. No. 5,772,845, issued on Jun. 30, 1998 to Farrington, Jr. et al., the disclosure of which is herein incorporated by reference to the extent it is non-contradictory herewith. Creped tissue production is disclosed in U.S. Pat. No. 5,637,194, issued on Jun. 10, 1997 to Ampulski et al.; U.S. Pat. No. 4,529,480, issued on Jul. 16, 1985 to Trokhan; U.S. Pat. No. 6,103,063, issued on Aug. 15, 2000 to Oriaran et al.; and, U.S. Pat. No. 4,440,597, issued on Apr. 3, 1984 to Wells et al., the disclosures of all of which are herein incorporated by reference to the extent that they are non-contradictory herewith. Also suitable for application of the above mentioned chemical additives are tissue sheets that are pattern densified or imprinted, such as the webs disclosed in any of the following U.S. Pat. No. 4,514,345, issued on Apr. 30, 1985 to Johnson et al.; U.S. Pat. No. 4,528,239, issued on Jul. 9, 1985 to Trokhan; U.S. Pat. No. 5,098,522, issued on Mar. 24, 1992; U.S. Pat. No. 5,260,171, issued on Nov. 9, 1993 to Smurkoski et al.; U.S. Pat. No. 5,275,700, issued on Jan. 4, 1994 to Trokhan; U.S. Pat. No. 5,328,565, issued on Jul. 12, 1994 to Rasch et al.; U.S. Pat. No. 5,334,289, issued on Aug. 2, 1994 to Trokhan et al.; U.S. Pat. No. 5,431,786, issued on Jul. 11, 1995 to Rasch et al.; U.S. Pat. No. 5,496,624, issued on Mar. 5, 1996 to Steltjes, Jr. et al.; U.S. Pat. No. 5,500,277, issued on Mar. 19, 1996 to Trokhan et al.; U.S. Pat. No. 5,514,523, issued on May 7, 1996 to Trokhan et al.; U.S. Pat. No. 5,554,467, issued on Sep. 10, 1996 to Trokhan et al.; U.S. Pat. No. 5,566,724, issued on Oct. 22, 1996 to Trokhan et al.; U.S. Pat. No. 5,624,790, issued on Apr. 29, 1997 to Trokhan et al.; and, U.S. Pat. No. 5,628,876, issued on May 13, 1997 to Ayers et al., the disclosures of all of which are herein incorporated by reference to the extent that they are non-contradictory herewith. Such imprinted tissue webs may have a network of densified regions that have been imprinted against a drum dryer by an imprinting fabric, and regions that are relatively less densified (e.g., "domes" in the tissue sheet) corresponding to deflection conduits in the imprinting fabric, wherein the tissue sheet superposed over the deflection conduits is deflected by an air pressure differential across the deflection conduit to form a lower-density pillow-like region or dome in the tissue sheet.

Various drying operations may be useful in the manufacture of the tissue products of the present invention. Examples of such drying methods include, but are not limited to, drum drying, through drying, steam drying such as superheated steam drying, displacement dewatering, Yankee drying, infrared drying, microwave drying, radiofrequency drying in general, and impulse drying, as disclosed in U.S. Pat. No. 5,353, 521, issued on Oct. 11, 1994 to Orloff and U.S. Pat. No. 5,598,642, issued on Feb. 4, 1997 to Orloff et al., the disclosures of both which are herein incorporated by reference to the extent that they are non-contradictory herewith. Other drying technologies may be used, such as methods employing differential gas pressure include the use of air presses as disclosed U.S. Pat. No. 6,096,169, issued on Aug. 1, 2000 to Hermans et al. and U.S. Pat. No. 6,143,135, issued on Nov. 7, 2000 to Hada et al., the disclosures of both which are herein incorporated by reference to the extent they are non-contradictory herewith. Also relevant are the paper machines disclosed in U.S. Pat. No. 5,230,776, issued on Jul. 27, 1993 to I. A. Andersson et al.

The tissue product may contain a variety of fiber types both natural and synthetic. In one embodiment the tissue product comprises hardwood and softwood fibers. The overall ratio of hardwood pulp fibers to softwood pulp fibers within the tissue product, including individual tissue sheets making up the product may vary broadly. The ratio of hardwood pulp fibers to softwood pulp fibers may range from about 9:1 to about 1:9, more specifically from about 9:1 to about 1:4, and most specifically from about 9:1 to about 1:1. In one embodiment of the present invention, the hardwood pulp fibers and softwood pulp fibers may be blended prior to forming the tissue web thereby producing a homogenous distribution of hardwood pulp fibers and softwood pulp fibers in the z-direction of the tissue web. In another embodiment of the present invention, the hardwood pulp fibers and softwood pulp fibers may be layered (stratified fiber furnish) so as to give a heterogeneous distribution of hardwood pulp fibers and softwood pulp fibers in the z-direction of the tissue web. In another embodiment, the hardwood pulp fibers may be located in at least one of the outer layers of the tissue product and/or tissue webs wherein at least one of the inner layers may comprise softwood pulp fibers. In still another embodiment the tissue product contains secondary or recycled fibers optionally containing virgin or synthetic fibers.

In addition, synthetic fibers may also be utilized in the present invention. The discussion herein regarding pulp fibers is understood to include synthetic fibers. Some suitable polymers that may be used to form the synthetic fibers include, but are not limited to: polyolefins, such as, polyethylene, polypropylene, polybutylene, and the like; polyesters, such as polyethylene terephthalate, poly(glycolic acid) (PGA), poly(lactic acid) (PLA), poly(β-malic acid) (PMLA), poly(ε-caprolactone) (PCL), poly(p-dioxanone) (PDS), poly(3-hydroxybutyrate) (PHB), and the like; and, polyamides, such as nylon and the like. Synthetic or natural cellulosic polymers, including but not limited to: cellulosic esters; cellulosic ethers; cellulosic nitrates; cellulosic acetates; cellulosic acetate butyrates; ethyl cellulose; regenerated celluloses, such as viscose, rayon, and the like; cotton; flax; hemp; and mixtures thereof may be used in the present invention. The synthetic fibers may be located in one or all of the layers and sheets comprising the tissue product.

The basis weight of tissue products treated in accordance with the present invention can also vary depending upon the ultimate use for the product. In general, the basis weight can range from about 6 gsm to 200 gsm and greater. For example, in one embodiment, the tissue product can have a basis weight of from about 6 gsm to about 80 gsm.

Since the at least one target delivery zone contained on the tissue product is located only on a portion of the surface area of the product, the tissue product retains most of its fluid handling capabilities. For example, the tissue product may have a specific liquid absorbent capacity of greater than about 4 g/g, such as from about 5 g/g to about 15 g/g. As used herein, the specific liquid absorbent capacity of a product refers to the absorbent capacity of the entire sheet including the treated region.

Figure 2:
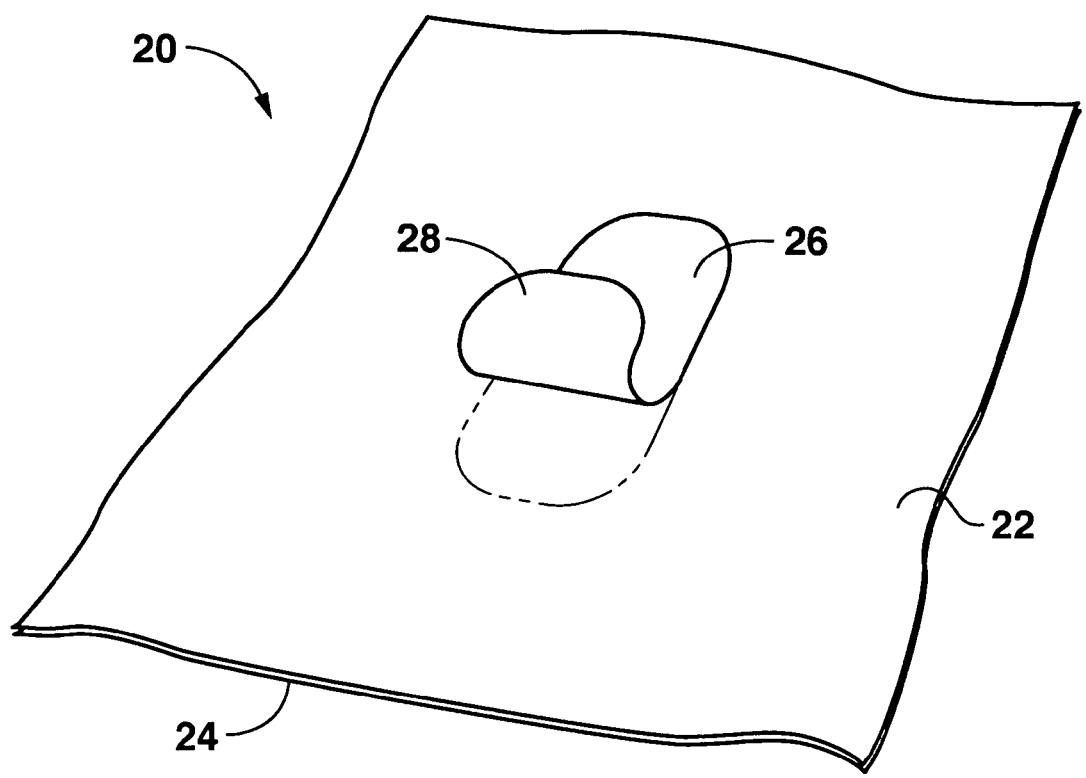
FIG. 2 is a perspective view of another embodiment of a tissue product made in accordance with the present invention.

Referring to FIG. 2, an alternative embodiment of a tissue product made in accordance with the present disclosure is shown. As illustrated, the tissue product 20 includes a first base web or ply 22 and a second ply 24. Located on the first ply 22 is a target delivery zone 26 to which an additive composition is applied. In this embodiment, in order to increase the amount of additive composition that is transferred to an opposing surface when the tissue product is wiped against the surface, the tissue product 20 includes a film 28 that is adhered to the base web 22 in the target delivery zone 26. The film 28 is positioned in between the base web 22 and the additive composition.

In general, any suitable film may be used that can be attached to the base web 22 and that causes greater amounts of the additive composition to transfer to an opposing surface. The film, for instance, may be made from a thermoplastic polymer. For example, the film may be made from a polyolefin such as polyethylene or polypropylene, from a polyester, from a polyamide, from a polyvinyl chloride, from combinations thereof, from copolymers thereof, and the like. In other embodiments, the film may comprise a biodegradable polymer from a renewable or non-renewable resource.

In order to attach the film 28 to the base web 22, any suitable adhesive material or method may be used. For example, the adhesive material may comprise a pressure sensitive adhesive. By placing a film below the additive composition, the film serves as a barrier and prevents the additive composition from being absorbed by the base web 22. In other methods, the film may be mechanically or thermally bonded to the sheet via processes such as embossing, heat embossing and the like. In general, any method known in the art for creating film laminates may be used. The additive may be applied to the film area prior to or after attaching to the basesheet.

Figure 3:
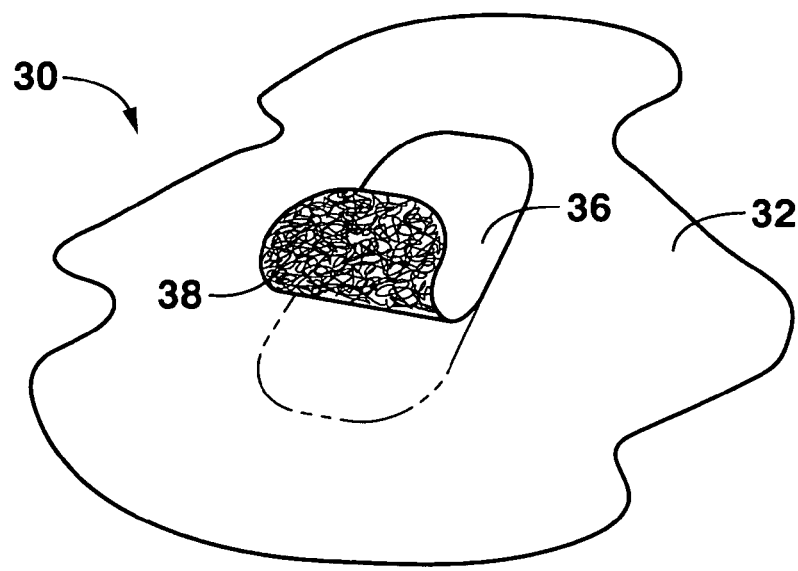
FIG. 3 is a perspective view of still another embodiment of a tissue product made in accordance with the present invention.

Referring to FIG. 3, another embodiment of a tissue product generally 30 made in accordance with the present disclosure is illustrated. The tissue product 30 as shown in FIG. 3 is similar to the tissue product 20 shown in FIG. 2. The tissue product 30 includes a target delivery zone 36 containing an additive composition positioned on a base web 32. In this embodiment, a nonwoven web 38 is positioned in between the additive composition and the base web 32.

The nonwoven web 38 can comprise any material that does not absorb appreciable amounts of the additive composition and allows the composition to transfer from the surface of the web. For example, in various embodiments, the nonwoven web 38 may comprise a bonded carded web, an airlaid web or a spunbond web. In one particular embodiment, the nonwoven web 38 comprises a meltblown web.

The nonwoven web 38 can be made from various polymeric materials. For example, the nonwoven web 38 may be made from a polyolefin such as polypropylene or polyethylene, from a polyamide, from a polyester, from combinations thereof, from copolymers thereof, and the like.

Similar to the film layer 28 as shown in FIG. 2, the nonwoven web 38 may be adhered to the base web 32 using a suitable adhesive material. Alternatively, the nonwoven web 32 may be bonded to the base web 32 using a mechanical attachment or through thermal bonding.

In the embodiments illustrated in FIGS. 2 and 3, the film 28 and the nonwoven web 38 are positioned on the same side of the base web as the additive composition. In an alternative embodiment, as shown in FIG. 4, a film or nonwoven web may be positioned on the opposite side of the base web.

Figure 4:
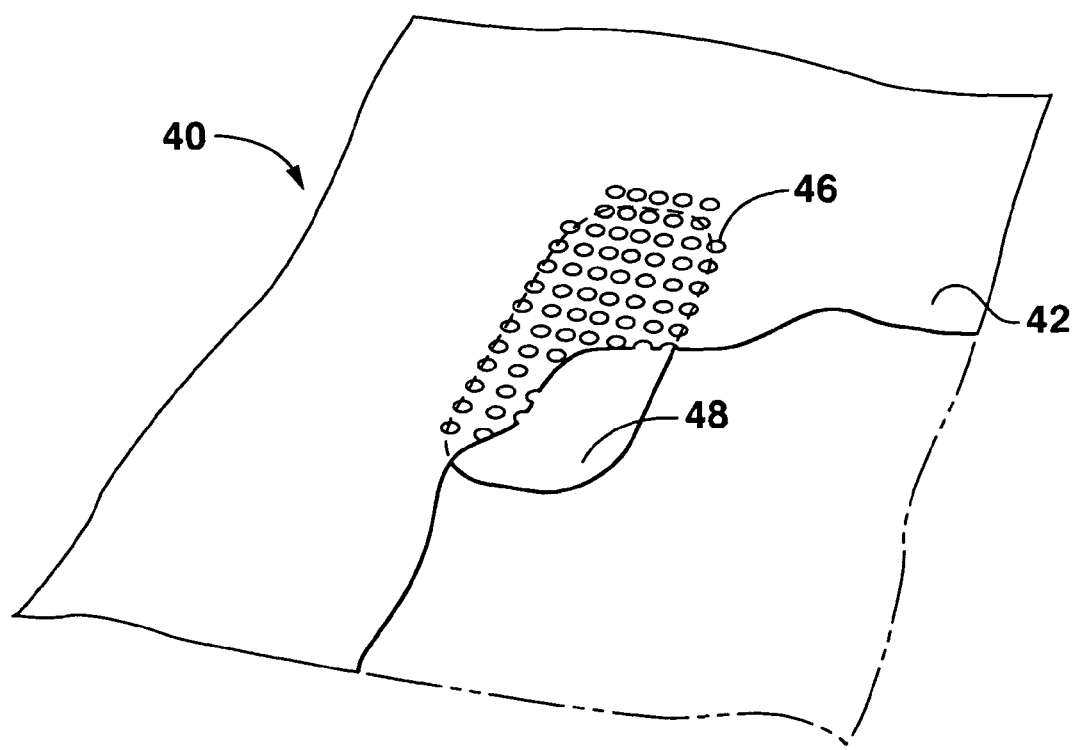
FIG. 4 is a perspective view with cutaway portions of another embodiment of a tissue product made in accordance with the present invention.

Referring to FIG. 4, a tissue product generally 40 is shown that includes a base web 42 defining a target delivery zone 46. An additive composition is applied on the base web in the target delivery zone 46. In this embodiment, a film or nonwoven web 48 is positioned on the opposite side of the base web 42 in forming the target delivery zone 46.

In the embodiment illustrated in FIG. 4, the film or nonwoven web 48 prevents the additive composition from bleeding through the base web 42. If desired, the base web 42 may be perforated in the target delivery zone so as to minimize the amount of additive composition that is absorbed by the base web.

Figure 5:
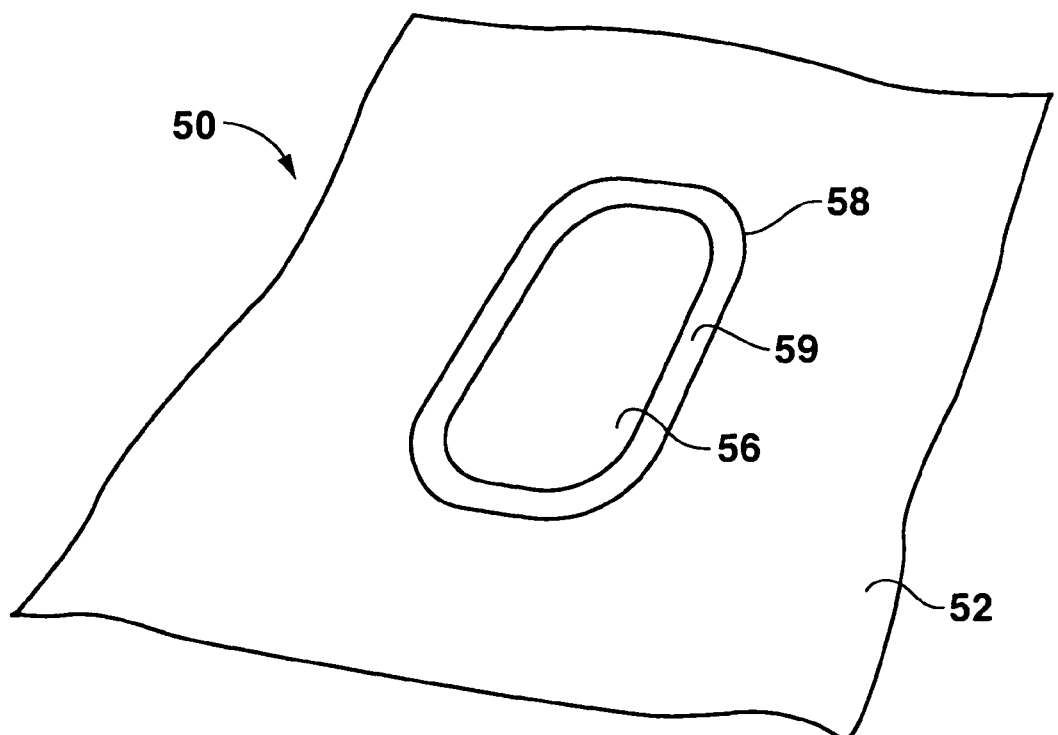
FIG. 5 is a perspective view of still another embodiment of a tissue product made in accordance with the present invention.

Referring to FIG. 5, still another embodiment of a tissue product generally 50 made in accordance with the present disclosure is shown. In this embodiment, the tissue product 50 includes a base web 52 defining a target delivery zone 56. An additive composition is applied to the target delivery zone. In order to ensure that the additive composition is efficiently transferred to an opposing surface during use, the additive composition is located on a modified portion 58 of the base web 52. The modified portion 58 may comprise, for example, any of the embodiments described above such as a polymer film, nonwoven web, or a topical treatment such as a sizing agent, resin or wax.

In the embodiment illustrated in FIG. 5, the modified portion 58 is larger than and surrounds the target delivery zone 56 forming a boundary 59. The boundary 59 separates the additive composition from the remainder of the base web 52. The boundary 59, for example, may be non-absorbent and therefore may prevent the additive composition from wicking or otherwise distributing in the X-Y direction. In other words, the boundary 59 prevents the additive composition from migrating onto the untreated portions of the base web 52. Use of a boundary 59 may be particularly beneficial when the additive composition comprises a liquid at room temperature.

As described above, the target delivery zone may be placed at any suitable location on the tissue product. At times it is desirable to have the target delivery zone located away from the area of the sheet used for absorption or cleaning. Typically the portion of the sheet used for absorbing and cleaning will be in the center of the sheet and therefore may be preferable to locate the target delivery zone on the periphery of the sheet away from the center. For example, in one embodiment, the additive composition may be located along a fold line so that the additive composition folds upon itself during packaging. For example, referring to FIGS. 6A and 6B, a tissue product generally 60 is shown including a base web 62 that contains a first fold line 72 and a second fold line 74. As illustrated, the target delivery zone 66 is positioned along the fold line 74 so that when the base web 62 is folded for packaging the additive composition folds upon itself. In this manner, the additive composition remains within the target delivery zone during packaging and does not become absorbed by the untreated portions of the base web.

In another embodiment, the tissue product may comprise a multi-ply tissue sheet. One of the outer plies of the tissue product has been selectively modified in order to reduce the affinity of the substrate for the additive composition. The additive composition is applied to the entire modified ply or a portion of the modified ply so as to create a product having enhanced transfer of the additive composition. A barrier ply may or may not be present between the two outer plies so as to prevent migration of the additive in the z-direction onto the unmodified ply.

Figure 6A:
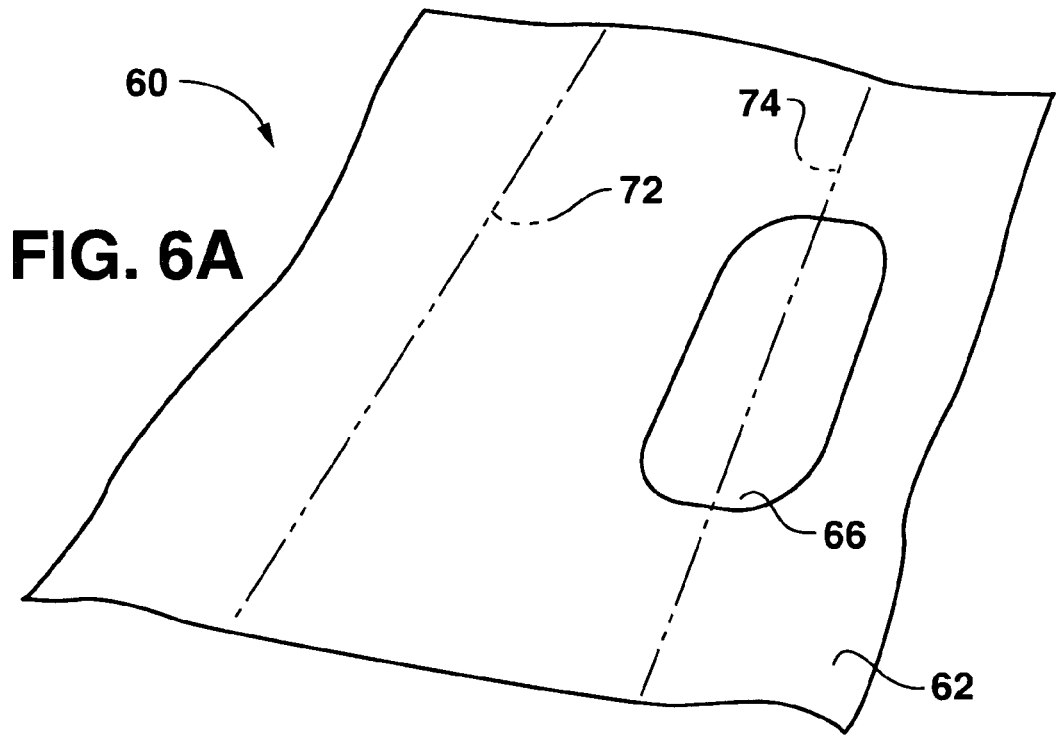
FIGS. 6A and 6B are perspective views of another embodiment of a tissue product made in accordance with the present invention in which the tissue product includes two fold lines.
Figure 6B:
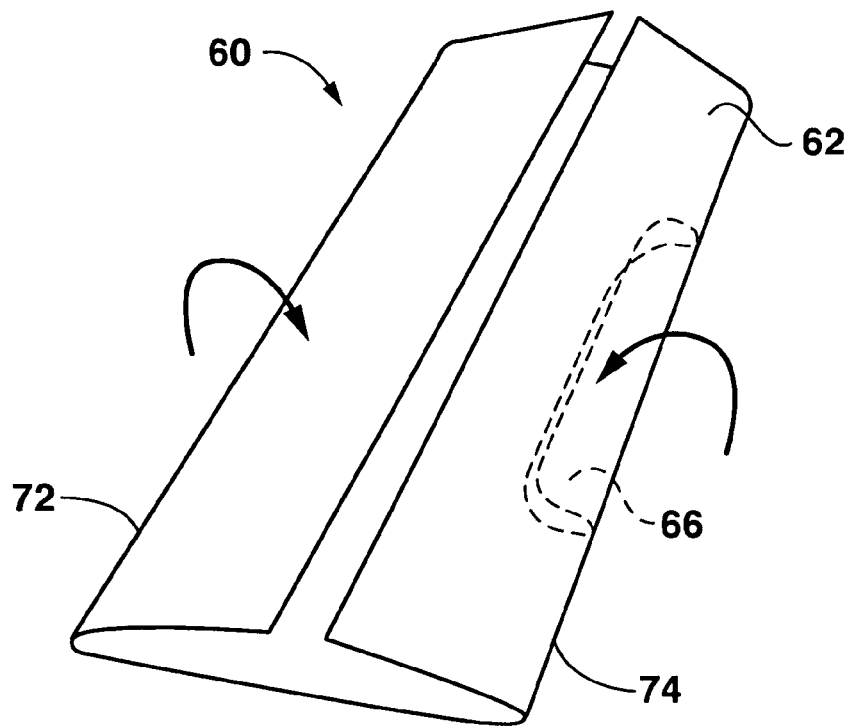

As shown in FIGS. 6A and 6B, the tissue product 60 includes a single target delivery zone 66. In an alternative embodiment, however, a first target delivery zone may be positioned along the fold line 74 while a second target delivery zone may be positioned along the fold line 72.

Figure 7A:
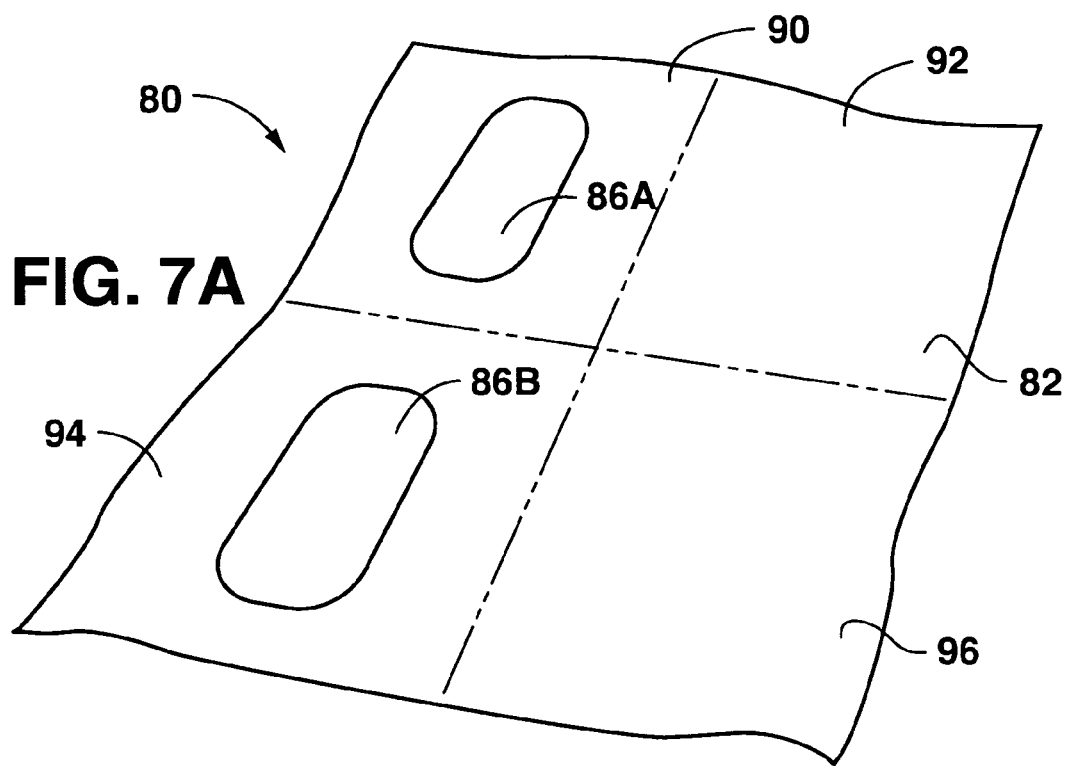
FIGS. 7A and 7B are perspective views of another embodiment of a tissue product made in accordance with the present invention in which the tissue product is divided into quadrants and an additive composition is applied to two of the quadrants.
Figure 7B:
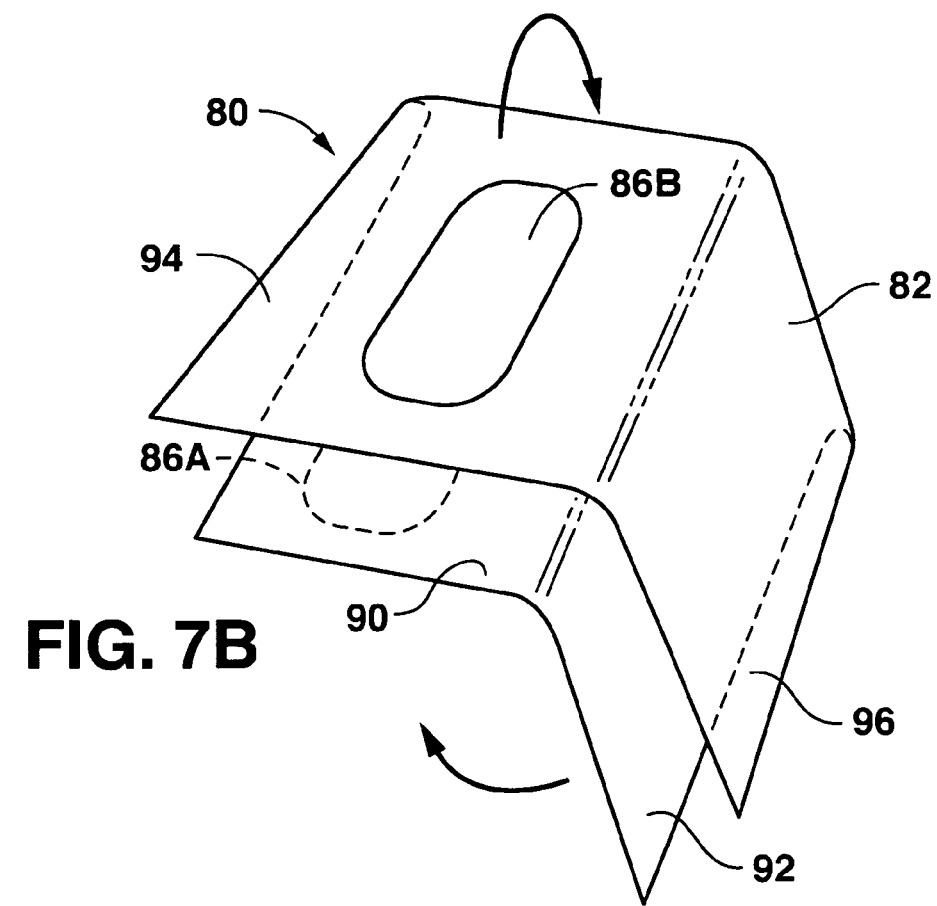

Referring to FIGS. 7A and 7B, still another embodiment of a tissue product generally 80 made in accordance with the present disclosure is illustrated. In this embodiment, the tissue product 80 includes a base web 82 that is folded into quadrants 90, 92, 94 and 96. The tissue product 80 includes a first target delivery zone 86A located on the quadrant 90 and a second target delivery zone 86B located on the quadrant 94. In certain embodiments, there may be some advantages and benefits to placing the target delivery zones on quadrants as shown in FIGS. 7A and 7B. For example, especially when the tissue product 80 is a facial tissue, consumers are known to fold the tissue in half to contain the nasal discharge within the inside of the tissue and then perform a final dry wiping exercise with the outside surface. In this case, they are likely to fold the tissue once more into quadrants. As shown in FIG. 7B, this procedure causes the target delivery zones 86B and 86A to contact the nose during this final wiping step.

In other embodiments, the target delivery zones may be placed in quadrants or at other suitable locations so that the two target delivery zones fold upon each other when the product is folded and packaged.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. A tissue product comprising:
a base web containing cellulosic fibers, the base web having a dry bulk density of at least about 2 cc/g, the base web having a first side and a second side;
a target delivery zone located on at least the first side of the base web, the target delivery zone comprising a portion of the total surface area of the first side and being located in a center and not on the periphery of the first side of the base web;
an additive composition applied to the target delivery zone on the base web;
wherein at least the first side of the base web has been modified prior to application of the additive composition at least in the target delivery zone in a manner that causes greater amounts of the additive composition to transfer to an opposing surface when the tissue product is wiped against the opposing surface the modification comprising adhering a polymeric film comprising a polyolefin, a nonwoven web containing synthetic fibers, a sizing agent, a wax, or a resin selected from the group consisting of starch, cellulose, polyhydroxyalcanoates and polylactides or mixtures thereof to at least the first side of the base web;
wherein the additive composition is applied over top of and forms a coating over the modified portion of the base web within the target delivery zone; and wherein the tissue product is a bath tissue, a facial tissue, a napkin, or a paper towel.

2. A tissue product as defined in claim 1, wherein the nonwoven web comprises a polyolefin.

3. A tissue product as defined in claim 1, wherein the polymeric film or nonwoven web comprises a biodegradable polymer.

4. A tissue product as defined in claim 1, wherein the first side of the base web has been modified by adhering a nonwoven web to one side of the base web, the nonwoven web comprising a spunbond web or a meltblown web.

5. A tissue product as defined in claim 1, wherein the first side of the base web has been modified to render the first side hydrophobic, the additive composition comprising a hydrophilic composition.

6. A tissue product as defined in claim 5, wherein the base web is a multi-ply product and the first side is an outer ply of the multi-ply product.

7. A tissue product as defined in claim 1, wherein the target delivery zone is visually differentiated from the remainder of the first side of the base web.

8. A tissue product as defined in claim 1, wherein the target delivery zone comprises less than about 70% of the surface area of the first side of the base web.

9. A tissue product as defined in claim 1, wherein the target delivery zone comprises from about 10% to about 60% of the surface area of the first side of the base web.

10. A tissue product as defined in claim 1, wherein the target delivery zone is surrounded at its perimeter by a barrier which underlies and is larger than the target delivery zone to prevent migration of the additive composition.

11. A tissue product as defined in claim 10, wherein the barrier comprises a polymer film or a nonwoven web.

12. A tissue product as defined in claim 1, wherein the tissue product has an absorbent capacity of at least 5 grams of water per gram of fiber.

13. A tissue product as defined in claim 1, wherein the tissue product comprises a multi-ply product, the base web comprising an outer ply of the tissue product.

14. A tissue product as defined in claim 1, wherein the additive composition is present in the target delivery zone in an amount of at least 25 gsm.

15. A tissue product as defined in claim 1 having two or more target delivery zones and wherein the target delivery zones comprise different additive compositions.

16. A tissue product as defined in claim 15, wherein the two or more target delivery zones are visually distinct from one another.

17. A tissue product as defined in claim 1, wherein the additive composition comprises a skin lotion.

18. A tissue product as defined in claim 1, wherein the additive composition comprises a silicone.

19. A tissue product as defined in claim 1, wherein the additive composition comprises a wax, an oil, and an alcohol.

20. A tissue product as defined in claim 1, wherein the additive composition comprises a sunscreen or an insect repellant.

21. A tissue product comprising:
a base web containing cellulosic fibers, the base web having a dry bulk density of at least about 2 cc/g, the base web having a first side and a second side;
a target delivery zone located on the first side of the base web, the target delivery zone comprising from about 10% to about 60% of the total surface area of the first side wherein the target delivery zone is located along a periphery and not in the center of the first side of the base web;
an additive composition applied only to the target delivery zone on the base web, the additive composition being present in the target delivery zone in an amount of at least 25 gsm; and
wherein at least the first side of the base web has been modified prior to application of the additive composition within the target delivery zone by adhering a polymeric film comprising a polyolefin, a nonwoven web containing synthetic fibers, a wax, or a resin selected from the group consisting of starch, cellulose, polyhydroxyalcanoates and polylactides or mixtures thereof and the additive composition is applied over top of and forms a coating over the modified portion of the base web in a manner that causes greater amounts of the additive composition to transfer to an opposing surface when the tissue product is wiped against the opposing surface; and
wherein the tissue product is a bath tissue, a facial tissue, a napkin, or a paper towel.

22. A tissue product as defined in claim 21, wherein the additive composition comprises a silicone.

23. A tissue product as defined in claim 21, wherein the additive composition comprises a wax, an oil, and an alcohol.

24. A tissue product as defined in claim 21, wherein the first side of the base web has been modified by adhering a nonwoven web to one side of the base web, the nonwoven web comprising a spunbond web or a meltblown web.

25. A tissue product as defined in claim 21, wherein the first side of the base web is only modified within the target delivery zone.

26. A tissue product as defined in claim 21, wherein the entire first side of the base web has been modified.

27. A tissue product as defined in claim 10, wherein the barrier comprises a boundary surrounding the perimeter of the target delivery zone which is free of the additive composition.

28. A tissue product as defined in claim 21, wherein the target delivery zone is surrounded at its perimeter by a barrier which underlies and is larger than the target delivery zone to prevent migration of the additive composition.

29. A tissue product comprising:
a base web containing cellulosic fibers, the base web having a dry bulk density of at least about 2 cc/g, the base web having a first side and a second side;
a target delivery zone located on at least the first side of the base web, the target delivery zone comprising a portion of the total surface area of the first side wherein the target delivery zone is asymmetrically located on the first side of the base web;
an additive composition applied to the target delivery zone on the base web;
wherein at least the first side of the base web has been modified prior to application of the additive composition at lest in the target delivery zone in a manner that causes greater amounts of the additive composition to transfer to an opposing surface when the tissue product is wiped against the opposing surface the modification comprising adhering a polymeric film comprising a polyolefin, a nonwoven web containing synthetic fibers, a sizing agent, a wax, or a resin selected from the group consisting of starch, cellulose, polyhydroxyalcanoates and polylactides or mixtures thereof to at least the first side of the base web;
wherein the additive composition is applied over top of and forms a coating over the modified portion of the base web within the target delivery zone; and wherein the tissue product is a bath tissue, a facial tissue, a napkin, or a paper towel.

30. A tissue product as defined in claim 26, wherein the base web includes a fold line, the target delivery zone being located along the fold line such that the additive composition is folded onto itself when the base web is folded.

31. A tissue product as defined in claim 21, wherein the base web includes a fold line, the target delivery zone being located along the fold line such that the additive composition is folded onto itself when the base web is folded.

32. A tissue product as defined in claim 21, wherein the base web includes four quadrants, the target delivery zone being present in only one or two of the quadrants.

33. A tissue product as defined in claim 26, wherein the base web includes four quadrants, the target delivery zone being present in only one or two of the quadrants.

34. A tissue product as defined in claim 1, wherein a weight per area of the additive composition is greater than a basis weight of the base web.

* * * * *